United States Patent [19]

LeVeen

[11] 4,377,573
[45] Mar. 22, 1983

[54] METHOD OF CONTROL OF GASTROINTESTINAL BLEEDING

[76] Inventor: Harry H. LeVeen, 321 Confederate Cir., Charleston, S.C. 29407

[21] Appl. No.: 867,501

[22] Filed: Jan. 6, 1978

Related U.S. Application Data

[63] Continuation of Ser. No. 670,969, Mar. 26, 1976, abandoned, which is a continuation-in-part of Ser. No. 259,279, Jun. 2, 1972, abandoned.

[51] Int. Cl.$^3$ .................... A61K 37/00; A61K 31/135
[52] U.S. Cl. ..................................... 424/177; 424/330
[58] Field of Search ................................ 424/330, 177

[56] References Cited

U.S. PATENT DOCUMENTS 3,371,080  2/1968  Boissonnas ..................... 260/112.5
3,671,636  6/1972  Saari ................................... 424/330

FOREIGN PATENT DOCUMENTS 1029034  5/1966  United Kingdom ................ 424/330
1076984  7/1967  United Kingdom ................ 424/177

OTHER PUBLICATIONS

*Remington's Pharmaceutical Sciences*, Martin et al, Mack Pub. Co., Easton, Pa. (1965) pp. 957–958.
*The American Journal of Surgery*, Feb. Issue pp. 144–159, 1972.
*Annals of Surgery*, vol. 175, #4, Apr. 1972, pp. 459–465.

*Primary Examiner*—Frederick E. Waddell
*Attorney, Agent, or Firm*—Brooks, Haidt, Haffner & Delahunty

[57] ABSTRACT

Norepinephrine has been found as useful in a method of treatment to control gastrointestinal bleeding when injected directly into the portal blood supply by direct injection into either the peritoneal cavity or the gastrointestine i.e. intragastrically. A dose unit for such administration is also described.

The method of administration described prevents systemic vasoconstriction and consequent serious hypertension in the patient. Passage through the liver inactivates the compound.

4 Claims, No Drawings

METHOD OF CONTROL OF GASTROINTESTINAL BLEEDING

RELATED APPLICATIONS

This application is a continuation of LeVeen application Ser. No. 670,969, filed Mar. 26, 1976, entitled METHOD OF CONTROLLING GASTROINTESTINAL BLEEDING, now abandoned, which is in turn a continuation-in-part of LeVeen application Ser. No. 259,279, filed June 2, 1972, entitled METHOD OF CONTROLLING GASTROINTESTINAL BLEEDING, now abandoned.

BACKGROUND OF THE INVENTION

Norepinephrine is known as a vasoconstrictor which exerts its effect by alpha receptor adrenergic stimulation. In this way and because of this activity it has principally been used for blood pressure supportive measures. It has also been used to block absorption of drugs such as novocaine. Norepinephrine is a sympathomimetic and produces a use in systemic blood pressure coupled with peripheral vasoconstriction when administered intravenously usually in the arm or leg of the patient. It can be orally administered and hence absorbed from the lining of the mouth tongue and throat and hence into the systemic circulation.

THE PRESENT INVENTION

It has now been discovered that severe gastrointestinal bleeding can be controlled without hypertensive side effects by direct intraperitoneal or intragastric injection of norepinephrine and other vasoconstrictors. It has been found that since such vasoconstrictors are absorbed into the portal system and inactivated by the liver they do not produce systemic hypertension when administered via the intraperitoneal route. The absorption which takes place is into the portal circulation only thereby avoiding the production of generalized hypertension which usually occurs when norepinephrine is administered in its conventional manner as a sympathomimetic by systemic intravenous infusion.

In accordance with the present invention the biochemistry of various vasoconstrictor drugs was evaluated with reference to the portal blood circulation and uncontrolled bleeding from organs fed by this system during surgery and otherwise. In all cases a single injectable dose of from 2 to 10 mg. of norepinephrine in isotonic saline as the free base and preferably a single injectable dose of 4 mg. of free base (8 mg. of bitartrate of same) in 250 cc. of isotonic salino were administered by injection intraperitonially, intragastrically and for comparison systemically into a vein in the arm of the patient. The results were compared both with respect to elevation of blood pressure and reduction in bloodloss in those patients suffering from loss of blood from the stomach vessels or other organs fed by the portal circulation. The rate of HCL secretion was also noted after such portal administration and found to be greatly reduced. By intragastric administration I mean direct feed into the stomach or portal circulation so as to by pass the systemic circulation on its input cycle and to pass through the liver for deactivation before entering the systemic circulation. This is not equivalent or in any manner similar to work done by Boissannas et al who have applied vasoconstrictors directly to bleeding vessels to reduce bleeding therefrom since this would elevate the systemic pressure and increase blood loss through opened vessels. Oral administration to reach the stomach is of no value because of absorption into the systemic circulation enroute to the stomach from the mucosa of the mouth tongue, throat et cetra.

The results of intraperitoneal injection into patients of the aforesaid dose of LEVOPHED was no change in systemic blood pressure, a brief rise and then a drop of portal pressure to about normal and no increase in portal vein lactate level in the blood. Thus patients experience an overall reduction in portal pressure alone. The measured operative blood loss in dogs was reduced by 90% in animals with such procedures as excision of the pyloric mucosa.

In a toxicity study in dogs the minimum lethal dose of norepinephrine was found to be greater than 24 milligrams in 250 cc of isotonic saline which caused neither hypertension nor death. The safe dose range is believed to be thus about 2 to 10 mg./250 cc. of saline but up to 20 cc/250 cc could probably be used.

In connection with the present invention the metabolism of certain hormones and drugs was studied with particular reference to the portal system and the portal circulation. In these experiments the umbilical vein in an adult patient was reopened to afford access to the portal system for injection of drugs and for removal of blood samples from the portal vein. In contrast when norepinephrine was administered intravenously in a systemic vein, e.g. in the arm, hypertension occurred immediately and continued as long as the administration was continued. Surprisingly, the same quantity of norepinephrine which produces an appreciable rise in systemic blood pressure under use according to prior practices had no effect on the blood pressure when injected into the portal system. This is believed to be due to the fact that the norepinephrine is inactivated in a single passage through the liver and since portal vein blood flows through the liver before entering the systemic circulation, no norepinephrine reached the systemic circulation.

Additional work was carried out with repository doses of norepinephrine injected into the peritoneal cavity of dogs and into their stomachs. The vasoconstriction which results from norepinephrine so significantly reduced absorption that complete inactivation by the liver took place after absorption into the portal circulation. Similar observations have been made using other vasoconstrictors such as vasopressin, angiotensin, etc., but norepinephrine had the best effects because of its short duration of action. Moreover, an experiment was carried out with dogs wherein bleeding stomach ulcers were created surgically and the animals have been treated by intraperitoneal or intragastric administration of norepinephrine. The control animals died promptly whereas the experimental animals survived. Thereafter human patients were treated with otherwise fatal general intestinal bleeding and the bleeding was arrested in about 75% of the cases when the method of the present invention was practiced. (LeVeen, H. H. et al., A Proposed Method to Interrupt Gastrointestinal Bleeding: Preliminary Report, Ann. of Surg. 175:4:459, April 1972. LeVeen et al., Control of Gastro-Intestinal Bleeding. Am. J. Surg. 123:154, 1972.)

The mechanism of cessation of bleeding was considered to be constriction involving the artery or arteriole which was bleeding with the constriction being of sufficient magnitude to favor clot formation. Experiments carried out animals with Pavlov pouches showed that the vasoconstriction caused by the local application of a variety of vasoconstrictors was capable of reducing hydrochloric acid secretion. Thus, the present invention also provides for the reduction of hydrochloric acid secretion in the control of peptic ulcers. Various vasoconstrictors were tested and norepinephrine was found to be effective, but of rather short action so that for the reduction of hydrochloric acid secretion long acting vasoconstrictors such as oxymetazoline or xylometazoline or tetrahydrozoline were found to be more effective and long lasting in bringing about controlled reduction of gastric hydrochloric acid output. Deprivation of the stomach of its blood supply by ligation of major arteries to the stomach is capable of reducing hydrochloric acid output. (LeVeen, H. H., The Effect of Surgical Interruption of Gastric Blood Flow upon Gastric Secretion and the Prevention of Experimental Peptic Ulcers. Surg. Gyn. & Obst. 1948, 86:164.) Moreover, Thompson and Vane showed that if maximum gastric secretion was induced in the cat by histamine injection, the output of hydrochloric acid was directly related to the amount of blood employed to perfuse the isolated stomach vessels (Thompson, J. E., Vane, J. R., Gastric Secretion Induced by Histamine and its Relationship to Blood Flow, J. Physiol., London, 121:433, 1953). This confirms the relationship of secretion and vascularity in experimental animals. Reference is made in this connection to the book by Wolf and Wolf, entitled "Human Gastric Function", published by Oxford University Press, 1943. Those authors made direct observations in humans with gastrostomy and confirmed that vascularity and secretion were indeed interrelated and that an increase in one causes an increase in the other (page 49).

The present invention therefore has as its major objective the control of gastrointestinal bleeding by the injection of vasoconstrictors into the peritoneal cavity and this is carried out with a dosage which depends generally on the severity of the gastrointestinal bleeding to be controlled, but may be in the range of 2 to 10 milligrams of the free base and preferably about 4 milligrams of the free base (8 mg of bitartrate). The active vasoconstrictor may be used in any of its known formulations as with a suitable carrier or solvent, but preferably in physiological saline solution. Alternatively angiotensin and vasopressin may be used in place of norepinephrine which is preferred. The invention further comprises a method for controlling hydrochloric acid secretion in peptic ulcers by reduction of the acid output by intragastric administration of one of the foregoing vasoconstrictors. In such case the dosage is adjusted so that the hydrochloric acid secretion is within normal limits, a condition which can be readily checked by simple test.

It is further to be understood that the norepinephrine or other vasoconstrictors can be used in the form of a pharmaceutically acceptable salt and in the case of the l-form of norepinephrine the salt is the bitartrate. Thus, when a vasoconstrictor is used in accordance with the present invention it is no longer a chemical mediator of postganglionic sympathetic nervous impulses and does not produce a rise in blood pressure coupled with peripheral vasoconstriction such as occurs during conventional use of norepinephrine.

I claim as my invention:

1. A method for the treatment and control of gastrointestinal bleeding and secretion of hydrochloric acid which comprises injecting intraperitoneally a single dose of from 2 to 10 milligrams of a vasoconstrictor compound selected from the group consisting of norepinephrin, vasopressin and angiotensin dissolved in a pharmaceutically acceptable liquid carrier.

2. A method according to claim 1 wherein the liquid carrier is isotonic saline in amount of from about 150 to 250 cc per single dose of vasoconstrictor compound.

3. A method according to claim 1 wherein the vasoconstrictor compound employed is norepinephrine.

4. A method according to claim 3 wherein the norepinephrine is injectably administered as a single dose in amount of 4 milligrams per 150 cc of isotonic saline.

* * * * *